United States Patent [19]

Okonogi et al.

[11] Patent Number: 4,601,985
[45] Date of Patent: Jul. 22, 1986

[54] **MICROORGANISM BELONGING TO *STREPTOCOCCUS THERMOPHILUS* AND A COMPOSITION CONTAINING SAID MICROORGANISM**

[75] Inventors: Shigeo Okonogi, Tokyo; Jyoji Ono, Chiba; Tsutomu Kudo, Yokohama; Akinori Hiramatsu, Hachioji; Susumu Teraguchi, Tama; Tomoko Yaeshima, Tokyo, all of Japan

[73] Assignee: Morinaga Milk Industry Co., Ltd., Tokyo, Japan

[21] Appl. No.: 547,825

[22] Filed: Nov. 2, 1983

[30] Foreign Application Priority Data

Nov. 9, 1982 [JP] Japan ................... 57-195375

[51] Int. Cl.$^4$ ............................... C12N 1/20
[52] U.S. Cl. ....................... 435/253; 435/42; 435/822; 435/885
[58] Field of Search ............... 435/42, 253, 822, 885; 426/34, 43, 61

[56] References Cited

U.S. PATENT DOCUMENTS 4,091,117 5/1978 Mutai et al. ..................... 426/43
4,339,464 7/1982 Vedamuthu ..................... 426/43

FOREIGN PATENT DOCUMENTS 2939528 4/1981 Fed. Rep. of Germany ........ 426/43

OTHER PUBLICATIONS

Mickelson, Journal of Bacteriology, 1967, No. 1, vol. 94, pp. 184–191.
O'Kane et al., Journal of Bacteriology, 1948, vol. 56, pp. 499–505.
Anders et al., Applied Microbiology, 1970, No. 4, vol. 19, pp. 608–612.
Terzaghi et al., Applied Microbiology, 1975, No. 6, vol. 29, pp. 807–813.
Bergey's Manual of Determinative Bacteriology, The Williams & Wilkins Co., Baltimore, 1974, p. 577.
Tinson et al., The Australian Journal of Dairy Technology, Mar., 1982, pp. 14–16.
Coventry et al., The Australian Journal of Dairy Technology, Dec. 1978, pp. 148–154.
Ozawa et al., Bulletin of the National Institute Agricultural Sciences, Series G (Animal Husbandry), No. 5, vol. 41, 1953, pp. 42–50.
Irie et al., Journal of the Agricultural Chemical Society of Japan, vol. 45, No. 9, 1971, pp. 423–425.
Suzuki et al., Japanese Journal of Zootechnical Science, 1982, vol. 53, No. 3, pp. 161–169.
Kaishi, Journal of the Agricultural Chemical Society of Japan, vol. 34, 1960, pp. 272–275, (partial translation).
Zasshi, Journal of the Pharmaceutical Society of Japan, vol. 99, No. 4, 1979, pp. 325–444.

*Primary Examiner*—Sam Rosen
*Assistant Examiner*—William J. Herald
*Attorney, Agent, or Firm*—Jordan and Hamburg

[57] ABSTRACT

This invention relates to a new microorganism belonging to *Streptococcus thermophilus* having an oxygen uptake ability of at least 30 nano moles per milligram of dried cell of said microorganism per minute which is defined by the quantity of oxygen consumption as determined by Warburg's manometric method, and to a microbial composition which comprises as main ingredients viable cell mass of (a) said microorganism and (b) bifidobacteria.

3 Claims, No Drawings

MICROORGANISM BELONGING TO *STREPTOCOCCUS THERMOPHILUS* AND A COMPOSITION CONTAINING SAID MICROORGANISM

This invention relates to a new microorganism belonging to *Streptococcus thermophilus* and having a high oxygen uptake ability, which will be hereinafter referred to as "the present microorganism" and to a composition containing a viable cell mass of the present microorganism.

An object of the present invention is to provide a new microorganism having a remarkable and significant high oxygen uptake ability.

Another object of the present invention is to provide a new microorganism which is capable of preventing anaerobic microorganisms from lethal inactivation when the latter are stored in the presence of the former under aerobic conditions.

A further object of the present invention is to provide a composition capable of preventing anaerobic microorganisms from lethal inactivation when a culture containing a viable cell mass of the anaerobic microorganisms is stored under aerobic conditions.

The term "thermophilus bacteria" used herein extensively refers to the well known microorganisms belonging to *Streptococcus thermophilus*. The term "Bifidobacteria" used herein extensively refers to microorganisms belonging to the genus Bifidobacterium.

The *thermophilus* bacteria are useful bacteria widely present in milk and milk products and are utilized as the starter bacteria for a variety of cheese including Swiss cheese, brick cheese and for yogurt (Takeo Nakanishi: "Microorganisms for Milk and Milk Products, page 22, published by Chikyu Publishing Co., Ltd. on Feb. 25, 1967).

Microbiological properties of thermophilus bacteria were described in detail in "Bergey's Manual of Determinative Bacteriology" compiled by R. E. Buchanan & N. E. Gibbons, 8th edition, pages 503-504, The Williams & Wilkins Company, Baltimore, U.S.A., 1974.

The oxygen uptake ability by the microorganisms belonging to the genus Streptococcus, for example, *Streptococcus agalactiae, Streptococcus cremoris, Streptococcus faeclis, Streptococcus faecium, Streptococcus lactis, Streptococcus liquefacience,* and *Streptococcus mastitidis*, was reported only in "Journal of Bacteriology," Volume 56, page 499 (1948); "Journal of Agricultural Chemical Society of Japan, "Volume 34, page 272 (1960); I. C. Gunsalus & R. Y. Stainer "The Bacteria", page 425, Academic Press Inc. (1961); "Journal of Bacteriology," Volume 94, page 184 (1967); "Applied Microbiology," Volume 19, page 608 (1970); "The Australian Journal of Dairy Technology," Volume 33, page 148 (1978); "Journal of Pharmaceutical Society of Japan," Volume 99, page 354 (1979).

According to these previous articles, the oxygen uptake abilities of *Streptococcus cremoris, Streptococcus lactis* and *Streptococcus faecium* were lower while those of the other four Streptococcus species were appreciably higher. The latter Streptococcus species were, however, incapable of being exploited for the food industry since they had traditionally not been considered to be dairy lactic acid bacteria.

"Australian Journal of Dairy Technology," volume 37, page 14 (1982), Tinson et al. reported that the oxygen uptake ability by the *thermophilus* bacteria was 7.3 $\mu$moles of oxygen molecules for 90 minutes per 12 mg of dried cell mass at 33.5° C. when skim milk containing 0.1% yeast extract was used as a substrate. This oxygen uptake ability, when converted to units of one minute per one mg of dried cell mass, was 6.76 nano moles of oxygen molecules which is very small. The oxygen uptake ability is hereinafter expressed in terms of nano moles as defined above.

The present inventors have made studies on symbiosis of the *thermophilus* bacteria and anaerobic microorganisms, and have isolated new strains of *Streptococcus thermophilus* having an oxygen uptake ability of at least 1.5 times as high as that of conventional *thermophilus* bacteria and have established the present invention.

The present invention will be described in detail below.

(1) Isolation of the new strains of the present invention belonging to *Streptococcus thermophilus*:

The strains belonging to *Streptococcus thermophilus* were isolated according to the following method as described by Ozawa et al (Bulletin of the National Institute of Agricultural Sciences, Series G (Animal Husbandry), No. 5, page 41 (1953)). The coagulated milk which was prepared by allowing raw milk to stand at 45°-50° C. for 4-5 days, or naturally acidified milk, were microscopically inspected. Those samples, in which existence of Streptococcus were confirmed, were inoculated with 10% (W/W) reconstituted skim milk sterilized at 115° C. for 15 minutes in a concentration of 5% (V/V) and were cultured at 45°-50° C. until coagulation was observed. Then cultures were serially transferred to the culture medium 2 to 3 times in the same manner as above, and one loopful of the culture was sampled and spread onto an M-17 agar medium (Applied Microbiology," Volume 29, No. 6, page 807 (1975) and incubated at 40° C. for 2-3 days. A number of strains were isolated from formed colonies. The bacteriological properties of the isolated strains were compared with those of the authentic *thermophilus* bacteria disclosed in the said "Bergey's Mannual of Determinative Bacteriology," and 40 strains of *Streptococcus thermophilus* were obtained.

(2) Oxygen uptake ability by the *thermophilus* bacteria:

40 strains belonging to said *Streptococcus thermophilus* which were isolated from the coagulated skim milk and naturally acidified milk, a strain of *Streptococcus thermophilus* 9Y (IDF Strain) which was identified to be an authentic *Streptococcus thermophilus* strain ("The Japanese Journal of Zootechnical Science," Volume 53, page 161, 1982) and *Streptococcus thermophilus* ATCC 19258 which was supplied from American Type Culture Collection (hereinafter referred to as "ATCC") were subjected to determination of the oxygen uptake ability in the following manner:

The cultures of these bacterial strains were inoculated in a nutrient medium containing 10 g Bactosoyton (Difco), 5 g yeast extract, 10 g lactose, 20 g sodium succinate-hexahydrate, 2 g $K_2HPO_4$ and 2 g $KH_2PO_4$ in 1 liter (Journal of the Agricultural Chemical Society of Japan," Volume 45, page 423, 1971) in a concentration of 5% (V/V), and subjected to stationary culturing at 37° C. for 16 hours. Cells were separated from the resulting culture medium by centrifugation, and washed with a sterilized physiological saline in a strile condition. Then, the cells were suspended in a sterilized physiological saline in a concentration of 3-5 mg of dry cell mass per ml. The oxygen uptake ability, which was defined by a quantity of oxygen consumption, of each strain was determined by a manometric method according to Warburg's procedure (Yoshikawa et al: Kagaku no Ryoiki ("Journal of Japanese Chemistry), special issue, No. 13, "Warburg's Manometer" published by Nankodo, February (1954)) as described below:

A vessel with two side compartments was used. One ml of the said bacterial suspension and 0.5 ml of sterilized 0.1M phosphate buffer solution of pH 6.0 were placed in the main compartment of a reactor vessel, and two aliquots of 0.75 ml of sterilized 20% (W/W) reconstituted skim milk were placed in two side compartments respectively as a substrate solution. A filter paper, impregnated with 0.2 ml of 20% (W/V) potassium hydroxide solution, was placed in an auxiliary compartment as a carbon dioxide absorber. The vessels were shaken for 5 minutes in advance in order to achieve temperature equilibrium, and then the substrate solution was added to the side compartments resulting in 10% concentration. The oxygen uptake rate was measured every 3 minutes and a maximum uptake rate was defined as the oxygen uptake ability.

The oxygen uptake ability by the tested strains is tabulated in Table 1.

TABLE 1

| Strain | Oxygen uptake ability in nano moles |
|---|---|
| 9Y | 19.8 |
| ATTC 19258 | 10.1 |
| STH - 01 | 30.0 |
| STH - 17 | 37.3 |
| STH - 23 | 42.3 |
| STH - 50 | 78.5 |
| STH - 15 | 14.7 |
| STH - 32 | 12.1 |
| other 34 strains | less than 18.5 |

As is obvious from Table 1, 36 strains among the separated 40 strains had an oxygen uptake ability of less than 18.5 nano moles, whereas the other four strains had an oxygen uptake ability of 30.0 to 78.5 nano moles. The standard strains of 9Y and ATCC 19258 had an oxygen uptake ability of 19.8 and 10.1 nano moles, respectively.

The present inventors attempted to measure the oxygen uptake ability of the four strains having a higher oxygen uptake ability according to the method by Tinson et al. for a comparative study with their observation. However, these four strains had such a remarkably high oxygen uptake ability that the procedure of determination after 90 minutes incubation by Tinson et al. was incapable of being applied. Therefore, the time periods which are required for absorption of 7.3 $\mu$moles of oxygen molecule, as described by Tinson et al., were measured according to the method by Tinson et al. According to Tinson et al., the value was 90 minutes, whereas those values of STH-01 and STH-23, of STH-17, and of STH-50 were 26, 28 and 21 minutes respectively (for comparison, those values of 9Y and of ATCC 19258 were 46 and 140 minutes respectively). It was concluded that the four strains of STH had a remarkably higher oxygen uptake ability than other strains.

(3) Bacteriological properties of the present strain:

The present inventors investigated bacteriological properties of these four strains of STH and found that the comprehensive bacteriological properties, other than a high oxygen uptake ability, were identical with those of the thermophilus bacteria disclosed in "Bergey's Manual of Determinative Bacteriology" as set forth below:

(A) Form of the bacterial cell aerobically incubated at 37° C. for 48 hours on an M-17 agar plate:
  a. Size (diameter): 0.7–0.9 $\mu$m
  b. Shape: spherical or ovoid, in pairs or chain
(B) Form of colonies aerobically formed at 37° C. for 48 hours on an M-17 agar plate:
  a. Shape: circular
  b. Elevation: convex circle
  c. Periphery: smooth
  d. Size (diameter): 0.5–1.5 mm
  e. Color tone: whitish and opaque
  f. Surface: smooth and lustrous
(C) Gas: non-producing
(D) Does not grow below 20° C.
(E) Grows at 45° C.
(F) Non-motile
(G) Endospore not formed.
(H) Gram-positive
(I) Benzidine-negative
(J) Catalase-negative
(K) Survives against heating at 65° C. for 30 minutes.
(L) Does not grow in the presence of 2% (W/V) sodium chloride.
(M) Does not grow in milk containing 0.1% (W/V) methylene blue.
(N) Does not grow at pH 9.6.
(O) Acid is produced from glucose, fructose, sucrose and lactose; no acid is produced from arabinose, xylose, raffinose, maltose, trehalose, inulin, mannitol, sorbitol, salicin and glycerol.
(P) Does not produce ammonia from arginine.

Even after serial transfer over 20 times in culturing these four strains, they had a high oxygen uptake ability. Thus the present inventors classified STH-01, STH-17, STH-23 and STH-50 as novel strains of Streptococcus thermophilus and they were respectively designated as Streptococcus thermophilus M-8202, Streptococcus thermophilus M-8203, Streptococcus thermophilus M-8204 and Streptococcus thermophilus M-8205 which were deposited in Fermentation Research Institute, Agency of Industrial Science and Technology on Oct. 22, 1982 with the respective accession numbers of FERM BP-351, FERM BP-352, FERM BP-353 and FERM BP-354.

A composition containing a culture of the present microorganisms will be described below:

The present microorganism has a high oxygen uptake ability as described above, and can uptake environmental oxygen even when stored under aerobic conditions, and thus can provide a favorable environment for viability existence of the coexistent anaerobic microorganism.

Anaerobic microorganisms are utilized for food, medicaments, and cattle and poultry feed etc. Bifidobacteria are physiologically and nutritionally favorable ingredient for applications described above while they are obligatory anaerobes and are less viable after storage of the composition for a prolonged period in the presence of oxygen. The present composition can remarkably prevent anaerobic microorganisms in it from lethal inactivation during storage owing to the high oxygen uptake ability of the present microorganism.

The present composition comprises a mixture of a cultrue containing a viable cell mass of anaerobic microorganisms, and a culture containing a viable cell mass of the present microorganism to a concentration at least $1 \times 10^8$, preferably $5 \times 10^8$ to $2 \times 10^9$ per gram of the mixture.

A culture containing a viable cell mass of anaerobic microorganisms includes, for example, a culture obtained by culturing the Bifidobacteria according to the well known method, a concentrate of such a culture obtained according to the well known method, cells separated from such a culture according to the well known method, or a suspension of such cells. A culture containing a viable cell mass of the present microorganism includes a culture obtained by culturing the present microorganism according to the well known method, a concentrate of such a culture obtained according to the well known method, cells separated from such a culture according to the well known method, or a suspension of such cells.

A culture containing a viable cell mass of anaerobic microorganisms is mixed with that containing a viable mass of the present microorganism to prepare a mixture containing the viable cells of the present microorganism to such a concentration as to prevent the anaerobic microorganisms from lethal inactivation.

A culture obtained by culturing the present microorganism in said manner contains, for example, $2 \times 10^8$ viable cells per gram of the culture when cultured in 10% (W/W) reconstituted skim milk medium at 37° C. for 16 hours, and $1 \times 10^9$ viable cells per gram of the culture when cultured in the nutrient broth ("Journal of the Agriculature Chemical Society of Japan," Volume 45, page 423 (1971)) at 37° C. for 16 hours. Thus, the amount of culture of the present microorganism to be added to the culture of anaerobic microorganisms can be determined from the number of viable cells in the culture of the present microoganism.

The present composition thus prepared effects less lethal inactivation of anaerobic microorganisms in it even after being stored under aerobic conditions, and thus can be utilized for fermented milk, beverages by lactic acid fermentation, medicaments for intestinal disorder, etc. in which the viable cells of anaerobic microorganism, for example, Bifidobacteria has an important significance.

An experimental result which shows an effect of the present microorganism on preventing anaerobic coexistent microorganisms from mortality is described in detail below.

(Test 1)

A. Bacterial strains:

The strains of *Streptococcus thermophilus*, 9Y and ATCC 19258, and M-8205 of the present invention, were used. As a typical anaerobic microorganisms, *Bifidobacterium longus* ATCC 15708 was used.

B. Preparation of starter cultures:

The starter cultures of the *thermophilus* bacteria and the present microorganism were prepared by inoculating subcultures of these microorganisms in 10% (W/W) reconstituted skim milk sterilized at 115° C. for 15 minutes in a concentration of 3% (V/V) and culturing them at 37° C. for 16 hours. The starter culture of the said *Bifidobacterium longum* was prepared by inoculating the subculture on 15% (W/W) reconstituted skim milk containing 0.25% (W/W) yeast extract sterilized at 115° C. for 15 minutes in a concentration of 10% (V/V) and culturing it at 37° C. for 5 hours.

C. Preparation of mixture:

The culture of said *Bifidobacterium longum* was prepared by homogenizing milk containing 0.1% (W/W) casamino acid, sterilizing the milk at 90° C. for 10 minutes, inoculating the starter culture of said *Bifidobacterium longum* prepared according to B above in a concentration of 5% (V/V) to conduct fermentation at 37° C. for 7 hours, and cooling the mixture immediately after fermentation.

The cultures of the *thermophilis* bacteria, and the present microorganism were respectively prepared by inoculating the starter cultures of the *thermophilis* bacteria and the present microorganism prepared according to B in a nutrient broth containing 1% (W/V) soy peptone, 0.5% (W/V) yeast extract, 1% (W/V) lactose, 2% (W/V) sodium succinate, 0.2% (W/V) dipotassium monohydrogen phosphate in a concentration of 5% (V/V), and culturing them at 37° C. for 16 hours. These cultures were separately centrifuged according to the ordinary method to collect cells of the *thermophilus* bacteria and the present microorganism. The collected cell pellets were washed with steriled physilogical saline and was suspended in steriled physiological saline to a concentration of $4 \times 10^{10}$/ml. The number of viable cells of the *thermophilus* bacteria and the present microorganism were measured according to the method described in D-b).

D. Test method:

The cell suspension of *thermophilus* bacteria and the present microorganism were separately added to the cultures of said *Bifidobacterium longum* respectively in concentrations of $3 \times 10^7$, $1 \times 10^8$, $5 \times 10^8$, and $2 \times 10^9$ per gram of the culture and uniformly mixed. The mixtures were filled in sterilized paper vessels having an appreciable air permeability and then the vessels were covered with lids.

The numbers of viable cells of said *Bifidobacterium longum* in the mixtures immediately after the preparation and in those which were stored at 5° C. for 7 days in a refrigerator were measured in the following manner. The survival fraction of said *Bifidobacterium longum* after the storage was calculated.

(a) Measurement of number of viable cells of said *Bifidobacterium longum*:

The starter cultures or the mixtures were decimally diluted with a diluent solution for anaerobic bacteria (Rinsho Kensa ("Journal of Medical Technology"), Volume 18, page 1163 (1974), and colony counting was conducted according to the method using an MGLP agar column for selective counting of the Bifidobacteria (Teraguchi et al: Shokuhin Eisei Zashi ("Journal of Food Hygienic Society of Japan"), Volume 23, page 39 (1982)).

(b) Measurement of number of viable cells of the *thermophilus* bacteria and the present microorganism:

Measurement was made according to the procedure of colony count in a standard nutrient agar medium containing BCP which was commercially available.

E. Test results:

The number of viable cells and survival fraction of said *Bifidobacterium longum* and the pH of the mixture are shown in Table 2.

TABLE 2

| Thermophilus bacteria | Thermophilus bacteria added | Bifidobacteria count | | | | |
|---|---|---|---|---|---|---|
| | | Immediately after preparation | | After storage | | |
| | | pH | Number of viable cells (per g) | pH | Number of viable cells (per g) | Survival fraction (%) |
| 9Y | $3 \times 10^7$ | 4.75 | $2.8 \times 10^9$ | 4.69 | $1.1 \times 10^7$ | 0.4 |
| | $1 \times 10^8$ | 4.72 | $2.8 \times 10^9$ | 4.68 | $2.8 \times 10^7$ | 1.0 |
| | $5 \times 10^8$ | 4.72 | $2.6 \times 10^9$ | 4.69 | $8.3 \times 10^7$ | 3.2 |
| | $2 \times 10^9$ | 4.69 | $2.4 \times 10^9$ | 4.63 | $1.5 \times 10^8$ | 6.3 |
| ATCC 19258 | $3 \times 10^7$ | 4.72 | $3.0 \times 10^9$ | 4.66 | $9.0 \times 10^6$ | 0.3 |
| | $1 \times 10^8$ | 4.73 | $2.7 \times 10^9$ | 4.68 | $2.4 \times 10^7$ | 0.9 |
| | $5 \times 10^8$ | 4.72 | $2.5 \times 10^9$ | 4.65 | $5.3 \times 10^7$ | 2.1 |
| | $2 \times 10^9$ | 4.70 | $2.5 \times 10^9$ | 4.65 | $1.2 \times 10^8$ | 4.8 |
| M-8205 | $3 \times 10^7$ | 4.73 | $2.9 \times 10^9$ | 4.65 | $6.4 \times 10^7$ | 2.2 |
| | $1 \times 10^8$ | 4.74 | $2.7 \times 10^9$ | 4.66 | $1.9 \times 10^8$ | 7.0 |
| | $5 \times 10^8$ | 4.70 | $2.3 \times 10^9$ | 4.63 | $3.8 \times 10^8$ | 16.5 |
| | $2 \times 10^9$ | 4.70 | $2.1 \times 10^9$ | 4.62 | $7.2 \times 10^8$ | 34.3 |

As is obvious from Table 2, the survival fraction of the said Bifidobacteria can be increased by coexistence of the *thermophilus* bacteria, while the effect of the present microorganism to stimulate the survival of said Bifidobacterium is distinctly remarkable.

The survival fraction of said Bifidobacteria in the presence of *thermophilus* bacteria 9Y and ATCC 19258, in a concentration of $1 \times 10^8$ and $2 \times 10^9$ per gram of the culture, was less than 1.0% and 6.3%, whereas the survival fractions were 7.0%, 16.5% and 34.3% in the presence of M-8205 of the present microorganism in a concentrations of $1 \times 10^8$, $5 \times 10^8$ and $2 \times 10^9$ per gram respectively. It was concluded that the survival fraction of said Bifidobacterium was elevated by 5 to 7 times in the presence of the present microorganism as compared with the case of the presence of the *thermophilus* bacteria.

Thus, it is evident that the present microorganism effects remarkably upon the survival of Bifidobacteria by addition of at least $1 \times 10^8$, preferably $5 \times 10^8$ to $2 \times 10^9$ per gram of the culture.

The effect of the present microorganism for various anaerobic microorganism is described below:

(Test 2)

A. Bacterial Strains:
Streptococcus thermophilus M-8205 (strain STH-50) as an example of the present microorganism, and Bifidobacterium bifidum ATCC 15696, Bifidobacterium infantis ATCC 15697, and Bifidobacterium adolescentis ATCC 15706 for typical anaerobic bacteria were used.

B. Preparation of starter cultures:
Same as in test 1.

C. Preparation of the mixtures:
Same as in test 1.

D. Test method:
Same as in test 1, except that the present microorganism was added in a concentration of $5 \times 10^8$ per gram of the cultures of the respective Bifidobacteria.

E. Test results:
The number of viable cells and the survival fractions of the respective Bifidobacteria and the pH of the mixtures are shown in Table 3.

TABLE 3

| Bifidobacteria | Immediately after preparation | | After storage | | |
|---|---|---|---|---|---|
| | pH | Number of viable cells (per g) | pH | Number of viable cells (per g) | Survival fraction (%) |
| *Bifidobacterium bifidum* ATCC 15696 | 4.80 | $9.5 \times 10^8$ | 4.72 | $1.0 \times 10^8$ | 10.5 |
| *Bifidobacterium infantis* ATCC 15697 | 4.61 | $2.5 \times 10^9$ | 4.55 | $2.8 \times 10^8$ | 11.2 |
| *Bifidobacterium adolescentis* ATCC 15706 | 4.82 | $3.0 \times 10^9$ | 4.73 | $4.6 \times 10^8$ | 15.3 |

As is obvious from Table 3, the survival fractions of all species of the Bifidobacteria, tested here, are more than 10% after reservation at 5° C. for 7 days when the present microorganism is added to the cultures in a concentration of $5 \times 10^8$ per gram of the cultures.

Thus, it is evident that the present microorganism effects remarkably upon the survival of various authentic Bifidobacteria and has an extensive protective function for viability of Bifidobacteria.

EXAMPLE 1

Ten kg of skim milk powder was dissolved in 90 kg of water, and the mixture was sterilized at 90° C. for 30 minutes and cooled. Then, 3 kg of a subculture of *Streptococcus thermophilus* M-8203 (STH-17) was inoculated in the mixture to conduct fermentation at 40° C. for 18 hours.

A subculture of *Bifidobacterium bifidum* ATCC 15696 was separately inoculated in 20 l of a culture medium containing 0.2% (W/W) of yeast extract and 12% (W/W) of reconstituted skim milk, sterilized at 90° C. for 30 minutes, in a concentration of 5% (W/W) to conduct fermentation at 37° C. for 8 hours.

Separately, 0.8 kg of pectine, 15 kg of sugar, 5 kg of cream of 50% (W/W) in fat content, and 0.2 kg of flavoring agent were dissolved in 59 kg of water, and the resulted syrup was sterilized at 85° C. for 10 minutes. Eighty kg of the present syrup was cooled to about 40° C., and was mixed with 100 kg of said fermented milk by *Streptococcus thermophilus* and 20 kg of said fermented milk by *Bifidobacterium bifidum* to obtain 200 kg of the mixture. The mixture was homogenized at 150 kg/cm², and filled in 350 individual paper containers of 500 ml in volume to produce commercial yogurt beverage containing viable cells of the present microorganism and the Bifidobacteria. The present yogurt beverage contained a viable cell mass of $2.4 \times 10^8$/ml of *Streptococcus thermophilus* and $8.5 \times 10^7$/ml of *Bifidobacterium bifidum*, and pH and a lactic acid concentration of 4.9 and 0.85% respectively. The number of viable cells of *Bifidobacterium bifidum* after being stored at 5° C. for 7 days was $1.3 \times 10^7$/ml., and the survival fraction was 15.3%.

EXAMPLE 2

Two hundred ml of a commercially available culture medium containing 1% (W/W) polypeptone, 1% (W/W) soy peptone, 0.5% (W/W) yeast extract, 1% (W/W) lactose, and 0.2% (W/W) monopotassium dihydrogen phosphate (pH 6.8) was sterilized at 90° C. for 30 minutes and cooled to 37° C. Then, 5 l of a subculture of *Streptococcus thermophilus* M-8205 (STH-50) was inoculated therein and incubated at 37° C. for 18 hours. Immediately after the incubation, the culture was cooled to about 5° C. and cells were collected with a Sharples centrifuge (15,000 rpm) and suspended in the same volume of physiological saline sterilized at 90° C. for 30 minutes as that of the culture medium, and centrifuged in the same manner to collect the cells again. The thus obtained cells were suspended in 10 l of a solution containing 10% (W/W) skim milk powder, 1% (W/W) sucrose, and 1% (W/W) sodium glutamate, sterilized at 90° C. for 30 minutes, and the suspension was freeze-dried according to the ordinary method to obtain about 1.2 kg of powders containing $4.5 \times 10^{10}$/g of viable cells.

Separately, a subculture of *Bifidobacterium infantis* ATCC 15697 was inoculated in 0.5 l of a culture medium, containing 0.2% (W/W) yeast extract and 12% (W/W) skim milk powder and was sterilized at 90° C. for 30 minutes, in a concentration of 5% (V/V) to conduct fermentation at 37° C. for 8 hours.

Separately, 7.5 kg of tomato puree, 0.2 kg of sugar, 10 kg of sodium chloride, 3 g of sodium glutamate and 10 g of flavor were mixed with 1.7 l of water, and the mixture was sterilized at 85° C. for 10 minutes and cooled. Then, 150 g of said powder of *Streptococcus thermophilus* and 500 g of fermented milk by *Bifidobacterium infantis* described above were added to the mixture, and mixed to prepare about 10 kg of fermented lactic beverage containing viable cells of the present microorganism and the Bifidobacterium. The beverage was filled in 40 individual paper containers of 200 ml in volume. The thus obtained fermented lactic beverage contained a cell mass of $6.2 \times 10^8$/ml of *Streptococcus thermophilus* and $1.3 \times 10^8$/ml of *Bifidobacterium infantis* at pH 4.60. The number of viable cells of *Bifidobacterium infantis* in the beverage, after being storage at 5° C. for 7 days, was $3.1 \times 10^7$/ml and the survival fraction was 23.8%.

What is claimed is:

1. A biologically pure microorganism belonging to *Streptococcus thermophilus* selected from the group consisting of *Streptococcus thermophilus* M-8202 (FERM BP-351), M-8203 (FERM BP-352), M-3204 (FERM 353), and M-8205 (FERM BP-354) and mixtures thereof which have an oxygen uptake ability of at least 30 nano moles per milligram of dried cells of said microorganism per minute which is defined by the quantity of oxygen consumption as determined by Warbur's manometric method.

2. A microbial composition which comprises as a main ingredient a biologically pure viable cell mass of (a) *Streptococcus termophilus* selected from the group consisting of *Streptococcus thermophilus* M-8202 (FERM BP-351), M-8203 (FERM BP-352), M-8204 (FERM BP-353), and M-8205 (FERM BP-354) and mixtures thereof which have an oxygen uptake ability of at least 30 nano moles per milligram of dried cells of said microorganism per minute which is defined by the quantity of oxygen consumption as determined by Warbur's manometric method and (b) bifidobacteria.

3. A microbial composition according to claim 2, wherein said *Streptococcus thermophilus* is at a concentration of $1 \times 10^8$ to $2 \times 10^9$ per gram of said composition.

* * * * *